(12) United States Patent
Greaves

(10) Patent No.: US 10,328,014 B2
(45) Date of Patent: Jun. 25, 2019

(54) COSMETIC PROCESS FOR ATTENUATING WRINKLES

(71) Applicant: L'OREAL, Paris (FR)

(72) Inventor: Andrew Greaves, Magny-le-Hongre (FR)

(73) Assignee: L'OREAL, Paris (FR)

( * ) Notice: Subject to any disclaimer, the term of this patent is extended or adjusted under 35 U.S.C. 154(b) by 35 days.

(21) Appl. No.: 15/536,320

(22) PCT Filed: Dec. 10, 2015

(86) PCT No.: PCT/EP2015/079224
§ 371 (c)(1),
(2) Date: Jun. 15, 2017

(87) PCT Pub. No.: WO2016/096594
PCT Pub. Date: Jun. 23, 2016

(65) Prior Publication Data
US 2017/0360677 A1 Dec. 21, 2017

(30) Foreign Application Priority Data
Dec. 16, 2014 (FR) ..................... 14 62485

(51) Int. Cl.
A61K 8/73 (2006.01)
A61Q 19/08 (2006.01)
C08B 37/08 (2006.01)
C08B 37/00 (2006.01)
A61K 8/91 (2006.01)
C08L 5/00 (2006.01)
C08L 5/04 (2006.01)
C08L 5/08 (2006.01)
C08L 5/10 (2006.01)
A61K 8/04 (2006.01)
A61N 5/06 (2006.01)
A61N 5/067 (2006.01)

(52) U.S. Cl.
CPC .............. A61K 8/735 (2013.01); A61K 8/042 (2013.01); A61K 8/73 (2013.01); A61K 8/731 (2013.01); A61K 8/733 (2013.01); A61K 8/91 (2013.01); A61N 5/062 (2013.01); A61N 5/0616 (2013.01); A61Q 19/08 (2013.01); C08B 37/0033 (2013.01); C08B 37/0069 (2013.01); C08B 37/0072 (2013.01); C08B 37/0075 (2013.01); C08B 37/0084 (2013.01); C08L 5/00 (2013.01); C08L 5/04 (2013.01); C08L 5/08 (2013.01); C08L 5/10 (2013.01); A61K 2800/81 (2013.01); A61N 2005/067 (2013.01); A61N 2005/0651 (2013.01); A61N 2005/0654 (2013.01); A61N 2005/0661 (2013.01); A61N 2005/0662 (2013.01)

(58) Field of Classification Search
CPC ...... C08L 5/04; C08L 5/08; C08L 5/00; C08L 5/10; A61K 8/735; A61K 2800/81; A61K 8/042; A61K 8/73; A61K 8/731; A61K 8/733; A61K 8/91; A61N 5/0616; A61N 5/062; A61Q 19/08; C08B 37/0033; C08B 37/0069; C08B 37/0072; C08B 37/0075; C08B 37/0084
See application file for complete search history.

(56) References Cited

U.S. PATENT DOCUMENTS

| 2010/0021404 A1 | 1/2010 | Delage-Grouiller et al. |
| 2011/0144563 A1 | 6/2011 | Samain et al. |
| 2015/0315434 A1* | 11/2015 | Steele .................. C09J 101/08 514/772.1 |

FOREIGN PATENT DOCUMENTS

| FR | 2 928 834 A1 | 9/2009 |
| JP | 2004 018841 A | 1/2004 |
| WO | WO-02/088189 A2 | 11/2002 |
| WO | WO-2014/081391 A1 | 5/2014 |
| WO | WO-2014/149469 A1 | 9/2014 |

OTHER PUBLICATIONS

Schante et al. Chemical modifications of hyaluronic acid for the synthesis of derivatives for a broad range of biomedical applications. Carbohydrate Polymers 85 (2011) 469-489. (Year: 2011).*
Yang et al. Research progress on chemical modification of alginate: A review. Carbohydrate Polymers 84 (2011) 33-39. (Year: 2011).*
Huerta-Angeles et al. Synthesis of highly substituted amide hyaluronan derivatives with tailored degree of substitution and their crosslinking via click chemistry. Carbohydrate Polymers 84 (2011) 1293-1300. (Year: 2011).*

(Continued)

Primary Examiner — Robert A Wax
Assistant Examiner — Olga V Tcherkasskaya
(74) Attorney, Agent, or Firm — Polsinelli PC

(57) ABSTRACT

The invention relates to a cosmetic process for caring for the skin, more particularly facial skin, in particular wrinkled skin, comprising the topical application to the skin of a cosmetic composition comprising a grafted polysaccharide polymer (I) and exposure of the treated skin to light radiation, polymer (I) being of formula:

PS—(CO—NH-L-X)$_a$(COOH)$_b$ in which PS denotes the basic backbone of the polysaccharide bearing the carboxylic acid groups;
L is a divalent hydrocarbon-based group containing from 1 to 20 carbon atoms;
X denotes a photoactive group of azide or diazirine type;
a denotes the content of COOH groups substituted with the group —NH-L-X;
b denotes the content of unsubstituted free COOH groups;
a being between 0.01 and 0.8; b being between 0.2 and 0.99; a+b=1

The invention also relates to the polymers (I) bearing a photoactive group X of diazirine type and to a composition comprising such a polymer in a physiologically acceptable medium.

30 Claims, No Drawings

(56) References Cited

OTHER PUBLICATIONS

Cumpstey. Chemical Modification of Polysaccharides. ISRN Organic Chemistry vol. 2013, Article ID 417672, 27 pages. (Year: 2013).*

Fan et al. Preparation and characterization of sodium alginate modified with collagen peptides. Carbohydrate Polymers 93 (2013) 380-385. (Year: 2013).*

Woo et al., "Injectable Photoreactive Azidophenyl Hyaluronic Acid Hydrogels for Tissue Augmentation", Macromolecular Research, vol. 22, No. 5, pp. 494-499 (2014).

* cited by examiner

COSMETIC PROCESS FOR ATTENUATING WRINKLES

CROSS REFERENCE TO RELATED APPLICATIONS

This application is a National Phase filing under 35 U.S.C. § 371 of PCT/EP2015/079224 filed on Dec. 10, 2015; and this application claims priority to Application No. 1462485 filed in France on Dec. 16, 2014 under 35 U.S.C. § 119. The entire contents of each application are hereby incorporated by reference.

The present invention relates to a process for attenuating wrinkles on the skin, using a composition comprising a polysaccharide polymer bearing a carboxylic acid group grafted with a particular photoactive group, and exposure of the treated skin to light. The invention also relates to novel polysaccharide polymers bearing a carboxylic acid group grafted with a particular photoactive group.

During the ageing process, various signs appear on the skin, which are very characteristic of this ageing, resulting in particular in a modification of skin structure and functions. The main clinical signs of skin ageing are in particular the appearance of fine lines and deep wrinkles, which increase with age.

It is known practice to treat these signs of ageing using cosmetic or dermatological compositions containing active agents capable of combating ageing, such as α-hydroxy acids, β-hydroxy acids and retinoids. These active agents act on wrinkles by eliminating dead skin cells and by accelerating the cell renewal process. However, these active agents have the drawback of only being effective for the treatment of wrinkles after a certain application time. Now, it is increasingly sought to obtain an immediate effect of the active agents used, rapidly resulting in smoothing-out of wrinkles and fine lines and in the disappearance of the signs of fatigue.

Polymers of hyaluronic acid grafted with photoactive groups are described in documents U.S. Pat. Nos. 5,563,056, 5,217,492 and 5,002,582 for surface treatment.

The article by H. D. Woo et al., *Injectable Photoreactive Azidophenyl Hyaluronic Acid Hydrogels for Tissue Augmentation*, Macromolecular Research, Vol. 22, No. 5, pages 494-499 (2014), describes hydrogels of hyaluronic acid grafted with an azidophenyl group, which are useful for filling wrinkles by injection into the skin.

The inventors have discovered that the topical application to the skin of a polysaccharide polymer bearing an acid group grafted with photoreactive groups of azide or diazirine type, combined with exposure of the treated skin to light radiation, forms a film that especially has an improved tensioning effect on the skin and thus makes it possible rapidly to attenuate wrinkles on the skin. The film obtained shows good resistance to water and to sweat. The tensioning effect of the film on the skin also shows good resistance to water and thus good persistence with respect to water, and also to sweat and sebum. The polymer deposit obtained after exposure to light is also resistant to the mechanical stresses of the skin (generated by the movements of the skin).

More specifically, a subject of the present invention is a process, in particular a cosmetic process, for caring for the skin, more particularly facial skin, in particular wrinkled skin, comprising:

(i) a step consisting in applying to the skin a composition, especially a cosmetic composition, comprising, in a physiologically acceptable medium, a polysaccharide polymer bearing a carboxylic acid group grafted with photoactive groups of azide or diazirine type of formula (I) as defined below;

(ii) a step consisting in exposing the skin to light radiation, preferably for at least 5 seconds. This step can be repeated several times during the day.

The process according to the invention is in particular intended for smoothing out human facial and/or body skin and/or for decreasing or effacing the signs of skin ageing, in particular for reducing or effacing wrinkles and/or fine lines on the skin.

The term "tensioning agent" means compounds that are capable of having a noticeable tensioning effect, i.e. of smoothing out the skin and rapidly, or even immediately, reducing the wrinkles and fine lines, or even making them disappear.

The tensioning effect may be characterized by means of an in vitro retraction test as described in Example 1.

The polysaccharide polymer bearing a carboxylic acid group grafted with photoactive groups of azide or diazirine type used in the process according to the invention corresponds to formula (I) below:

in which PS denotes the basic backbone of a polysaccharide bearing the carboxylic acid groups;

L is a linear, branched or cyclic, saturated or unsaturated divalent hydrocarbon-based group comprising from 1 to 20 carbon atoms, preferably from 2 to 10 carbon atoms, which may be interrupted with one or more non-adjacent heteroatoms chosen from sulfur, oxygen, or an —NH—, —COO—, —CONH—, —O—CO—NH— or —NH—CO—NH— group, said divalent group possibly being substituted with one or more groups chosen from hydroxyl, amine, thiol, carboxylic acid, amide and cyano groups;

X denotes a photoactive group of azide or diazirine type;

a denotes the content of COOH groups substituted with the group —NH-L-X;

b denotes the content of unsubstituted free COOH groups;

a being between 0.01 and 0.8; b being between 0.2 and 0.99;

a+b=1.

For example, when a=b=0.5, this means that half of the carboxylic acid groups of the polysaccharide are grafted with the group —NH-L-X and the other half of the carboxylic acid groups are not grafted, corresponding to the grafted polymer of formula

Preferably, a is between 0.1 and 0.6; b is between 0.4 and 0.9. Preferentially, a is between 0.15 and 0.5; b is between 0.5 and 0.85.

The polysaccharide comprises, in addition to the carboxylic acid groups, hydroxyl groups and optionally additional groups such as amino (—$NH_2$) and aminoacetyl (—NHAc). These hydroxyl groups and these additional groups form part of the basic backbone of the polysaccharide bearing the carboxylic acid groups.

The polysaccharide bearing a carboxylic acid group may comprise one or more units chosen from uronic acid, glucuronic acid and mannuronic acid, preferably uronic acid.

The polysaccharide bearing a carboxylic acid group used according to the invention may be chosen from hyaluronic acid, chondroitin, chondroitin sulfate, alginic acid, heparin, heparin sulfate and xanthan gum.

Preferably, the polysaccharide bearing a carboxylic acid group is hyaluronic acid or alginic acid, preferentially hyaluronic acid.

Hyaluronic acid is a linear glycosaminoglycan composed of repeating D-glucuronic acid and N-acetyl-D-glucosamine units linked together via alternating beta-1,4 and beta-1,3 glycosidic linkages.

Advantageously, the polysaccharide bearing a grafted carboxylic acid group has a weight-average molecular weight ranging from 5000 daltons to 1 000 000 daltons, preferably ranging from 10 000 daltons to 500 000 daltons and even more preferentially ranging from 15 000 daltons to 350 000 daltons. The molecular weight can be determined in particular by liquid chromatography, the eluent being 0.1 M sodium chloride and 330 mg/l of sodium azide in water, with dextran as standard, and Wyatt Optilab T-Rex refractometer and Wyatt Dawn-Heleos II light scattering detectors.

Preferably, the polysaccharide bearing a grafted carboxylic acid group is a grafted hyaluronic acid comprising grafted units of formula (II) below:

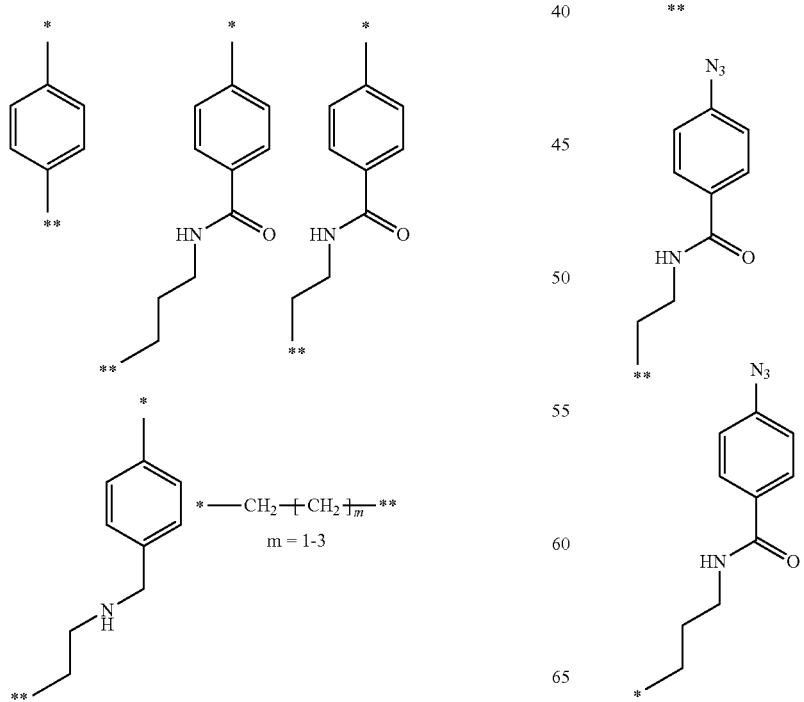

(II)

in which L, X, a and b have the meanings described previously, n especially being such that the grafted polymer has a molecular weight as defined previously.

Preferably, the group L is chosen from the following groups:

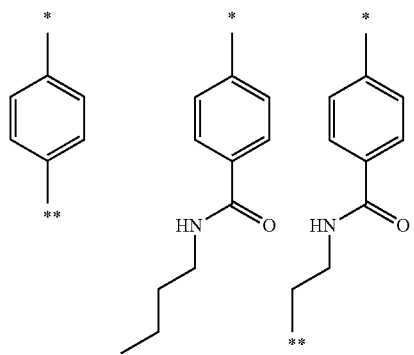

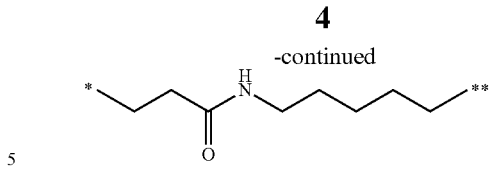

* representing the bond with the photoactive group X
** representing the bond with the amide group of the polymer The photoactive group X may be chosen from the following groups:

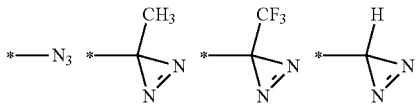

As examples of groups X-L-, mention may be made of the following groups:

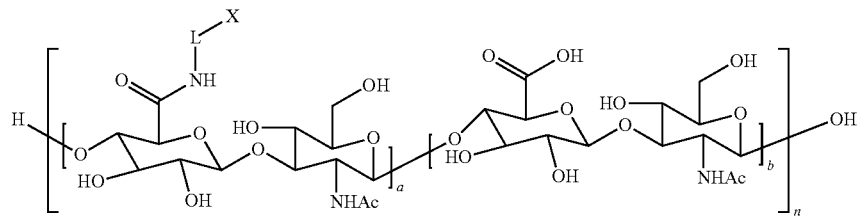

(i)

(ii)

(iii)

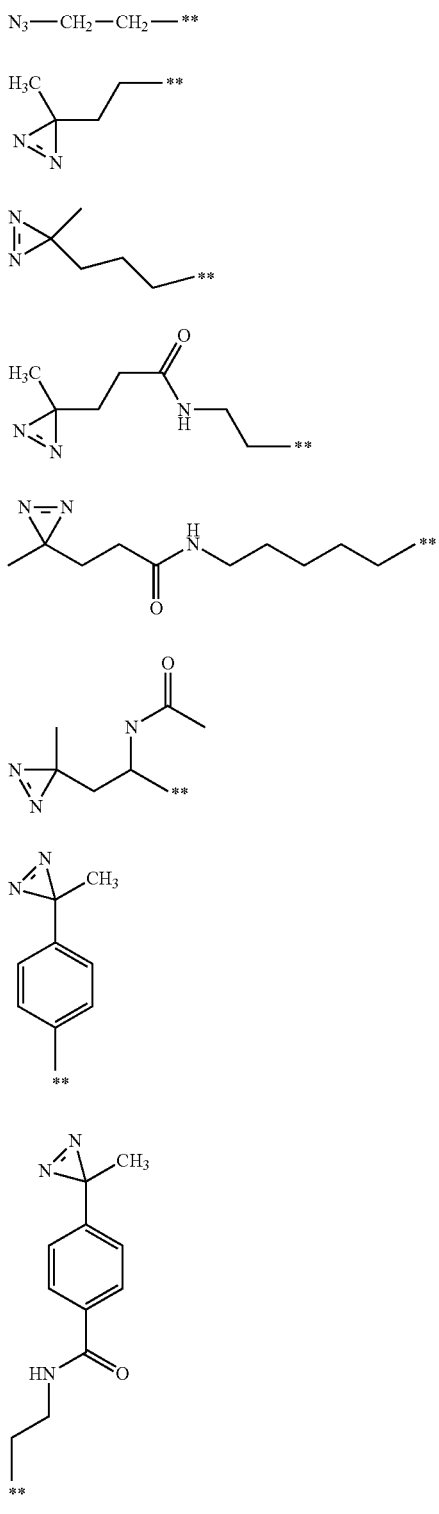

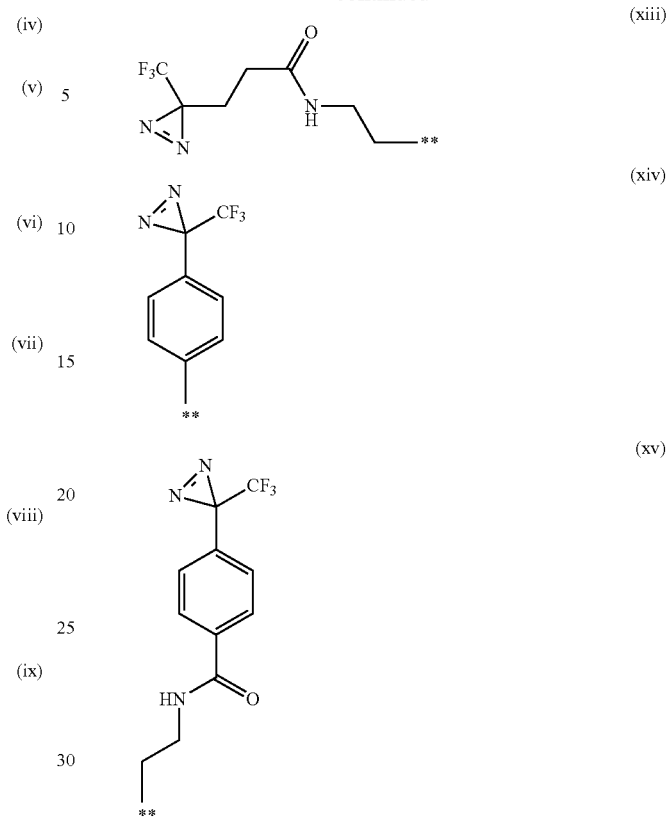

** representing the bond with the amide group of the polymer

Groups (i), (iii) and (viii) are preferred, and more particularly groups (i) and (iii).

The grafted polysaccharides used according to the invention may be prepared especially by activation of the carboxylic acid groups by reaction with a carbodiimide (A) such as 1-ethyl-3-(3-dimethylaminopropyl)carbodiimide hydrochloride or a dialkoxytriazine (A') such as 4-(4,6-dimethoxy-1,3,5-triazin-2-yl)-4-methylmorpholinium chloride to form an intermediate compound (B), followed by reaction with an amine of formula X-L-NH$_2$ (C) to form compound (I). Advantageously, the carbodiimide may be combined with an additional activator such as N-hydroxysuccinimide or N-hydroxysulfosuccinimide.

The grafting reaction of amine to the carboxylic acid of hyaluronic acid is described, for example, in the article: A systematic analysis of DMTMM vs DC/NHS for ligation of amines to Hyaluronan in water, Carbohydrate Polymers, 108 (2014), 239-246. DMTMM refers to activation of carboxyl groups with 4-(4,6-dimethoxy-1,3,5-triazin-2-yl)-4-methyl-morpholinium chloride and EDC/NHS refers to activation of carboxyl groups with N-(3-dimethylaminopropyl)-N'-ethyl-carbodiimide hydrochloride and N-hydroxysuccinimide.

The synthetic scheme for the reaction is as follows:

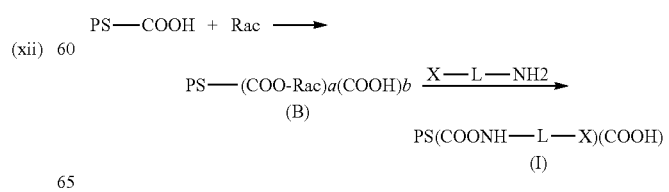

Rac representing a carboxylic acid-activating group, for instance carbodiimides or dialkoxytriazines.

Examples of compounds Rac with the corresponding coupling products B obtained are cited below:

| Activator | Compound (B) with 100% grafting |
|---|---|
| 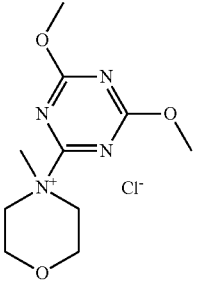 [SMILES: COc1nc(OC)nc([N+]2(C)CCOCC2)n1 ; [Cl-]]<br>4-(4,6-dimethoxy-1,3,5-triazine-2-yl)-4-methylmorpholinium chloride | 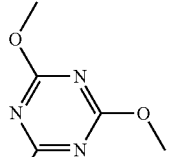 |
| 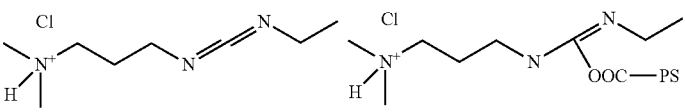<br>1-ethyl-3-(3-dimethylaminopropyl)carbodiimide hydrochloride | |

Compound B then reacts with the compound X-L-NH2 to form the product of formula (I).

Certain compounds X-L-NH2 are available, such as the compounds bearing a group X-L-(i) [CAS: 6427-66-3] and (v) [CAS: 87156-40-9].

The compounds X-L-NH$_2$ containing groups (iii) and (iv) may be prepared according to the reaction scheme below. This reaction is known to those skilled in the art and described in the article *Heterocycles*, 35 (2), 997-1004, 1993.

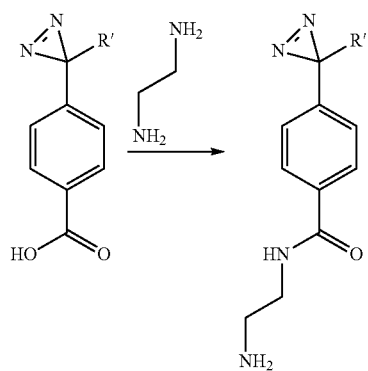

R' representing a methyl or trifluoromethyl group.

Similarly, the compound X-L-NH$_2$ containing group (ii) may be prepared according to the reaction scheme below using 4-amidobenzoic acid [CAS 6427-66-3].

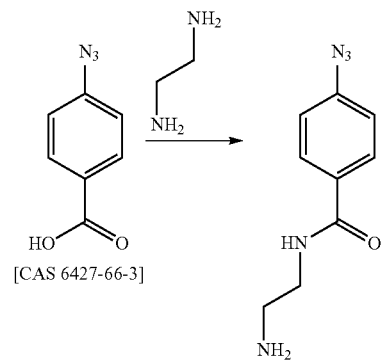

Similarly, the compounds X-L-NH$_2$ containing groups (vii) and (viii) may be prepared according to the reaction scheme below, the reagents being commercially available (from the company Fischer Scientific).

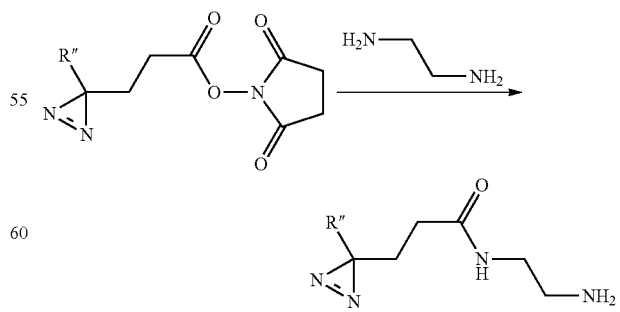

R" representing a methyl or trifluoromethyl group.

The compounds X-L-NH$_2$ containing groups (vi) and (ix) may be prepared according to the reaction scheme below, which consists in replacing a halogen with a primary amine. This reaction is known to those skilled in the art and described in numerous publications, for example in March's Advanced Organic Chemistry: Reactions, Mechanisms, and Structure, ISBN-13: 978-0470462591. The reagents are commercially available (from the company Sigma Aldrich).

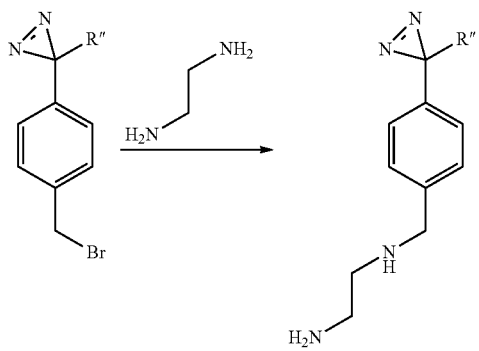

Advantageously, the polysaccharide polymer bearing a grafted carboxylic acid group has a degree of grafting with photoactive groups ranging from 1% to 80%, preferably ranging from 10% to 60%, and preferentially ranging from 15% to 50%. The degree of grafting corresponds to the mole percentage of COOH groups of the polysaccharide that are grafted with a photoactive group —NH-L-X.

By way of example, a degree of grafting of 50% corresponds to half of the COOH groups of the polysaccharide grafted with a photoactive group —NH-L-X.

The grafted polymers (I) comprising an aziridine group are novel compounds.

A subject of the invention is thus also the compounds of formula (I) described previously, and in particular those of formula (I') below:

PS—(CO—NH-L-X)a(COOH)b in which PS denotes the basic backbone of the polysaccharide bearing the carboxylic acid groups;

L is a linear, branched or cyclic, saturated or unsaturated divalent hydrocarbon-based group comprising from 1 to 20 carbon atoms, preferably from 2 to 10 carbon atoms, which may be interrupted with one or more non-adjacent heteroatoms chosen from sulfur, oxygen, or —NH—, —COO—, —O—CO—NH— or —NH—CO—NH— groups, said divalent group being optionally substituted with one or more groups chosen from hydroxyl, amine, thiol, carboxylic acid, amide and cyano groups;

X denotes a photoactive group of diazirine type a denotes the content of COOH groups substituted with the group —NH-L-X b denotes the content of unsubstituted free COOH groups a being between 0.01 and 0.8; b being between 0.2 and 0.99 a+b=1.

The preferred meanings described previously for compounds (I) also apply to compounds (I').

A subject of the invention is also a composition comprising, in a physiologically acceptable medium, a grafted polysaccharide (I') as defined previously.

The composition used according to the invention is generally suitable for topical application to the skin and thus generally comprises a physiologically acceptable medium, i.e. a medium that is compatible with the skin and/or its integuments. It is preferably a cosmetically acceptable medium, i.e. a medium which has a pleasant colour, odour and feel and which does not cause any unacceptable discomfort (stinging, tautness or redness) liable to discourage the consumer from using this composition.

The grafted polysaccharide (I) or (I') may be present in the composition according to the invention in a content ranging from 0.1% to 10% by weight, especially ranging from 0.3% to 10% by weight, preferably ranging from 0.5% to 10% by weight, preferentially ranging from 1% to 8% by weight and more preferentially ranging from 1% to 6% by weight, relative to the total weight of the composition. In particular, the composition preferably comprises at least 3% by weight of grafted polysaccharide (I) or (I').

The composition according to the invention may be in any galenical form conventionally used for topical application and especially in the form of dispersions of aqueous gel or lotion type, emulsions of liquid or semi-liquid consistency of the milk type, obtained by dispersing a fatty phase in an aqueous phase oil-in-water (O/W) or vice versa water-in-oil (W/O), or suspensions or emulsions of soft, semi-solid or solid consistency of the cream or gel type, or alternatively multiple emulsions water-in-oil-in-water (W/O/W) or oil-in-water-in-oil (O/W/O), microemulsions, vesicular dispersions of ionic and/or nonionic type, or wax/aqueous phase dispersions. These compositions are prepared according to the usual methods.

According to one preferred embodiment of the invention, the composition is in the form of an O/W emulsion or an aqueous gel.

Advantageously, the composition used according to the invention comprises water, in particular in a content which may range from 10% to 99% by weight and preferably ranging from 50% to 99% by weight, relative to the total weight of the composition.

The composition used according to the invention may also contain one or more adjuvants commonly used in the cosmetic field, such as emulsifiers, preserving agents, sequestrants, fragrances, thickeners, oils, waxes or film-forming polymers.

Needless to say, a person skilled in the art will take care to select this or these optional additional compound(s), and/or the amount thereof, such that the antiwrinkle properties of the composition according to the invention are not, or are not substantially, adversely affected by the envisaged addition.

Advantageously, for the process according to the invention, it is possible to apply 0.001 g to 0.5 g of cosmetic composition comprising the polysaccharide polymer bearing a grafted carboxylic acid unit, especially 0.005 g to 0.1 g of composition, per cm² of skin.

The process according to the invention also comprises a step consisting in exposing the skin to light radiation preferably having a wavelength of between 360 nm and 600 nm.

It is possible to perform this step consisting in applying light radiation before, after or at the same time as (simultaneously with) the step consisting in applying the composition comprising the polysaccharide polymer bearing a grafted uronic acid unit. Preferably, the two steps are carried out simultaneously.

Preferentially, in a first stage, the composition comprising the polysaccharide polymer bearing a grafted uronic acid unit is applied to the skin, and then, in a second stage, light radiation is applied to the skin.

It is possible to perform a step of rinsing, for example with water, of the skin between each step of the process.

Preferably, the light radiation used in the process according to the invention has a wavelength of between 400 nm and 480 nm.

The light radiation preferably has a flux (amount of energy per unit surface area) ranging from 0.1 J/cm² to 100 J/cm² and preferably ranging from 1 J/cm² to 10 J/cm².

The light radiation may be continuous or non-continuous light.

The light radiation may be natural light (daylight).

The light radiation may be generated by a device, such as arc lamps such as xenon lamps and mercury lamps; fluorescent lamps; incandescent lamps such as halogens; LEDs and lasers.

Mention may be made especially of goLITE BLU from the company Philips, the lamp Energylight HF 3319/01 from the company Philips, the lamps Dayvia White and Messa from the company Solvital, the lamp Lumino Plus from the company Lanaform, the lamp Medibeam from the company Medibeam, the lamp M-LED 01 from the company Meimed, the lamp Lifemax Light Pod from the company Lifemax, the lamp Lite-Pad from the company Reicorp, and the lamp Camag Box 3 (4×8 W) from the company Camag.

The exposure time of the treated skin to the light radiation provided by a device is preferably at least 5 seconds. Preferably, this exposure time can range from 10 seconds to 15 minutes, in particular between 15 seconds and 10 minutes, even better still between 20 seconds and 5 minutes, regardless of the order of the steps (one before the other or simultaneous).

By way of example, in the case of simultaneous application of the light radiation provided by a device and of the composition comprising the polysaccharide polymer bearing a grafted uronic acid unit, the light-exposure time may advantageously range from 5 seconds to 15 minutes. It is possible to perform rinsing of the composition.

By way of example, in the case of application of the composition according to the invention followed by exposure to light radiation provided by a device, the light-exposure time may advantageously be between 5 seconds and 15 minutes. It is possible to leave the composition used according to the invention in place for a period of 1 second to 3 hours, before performing the step of applying the light radiation. It is possible to perform rinsing of the composition, after the step of exposure to light radiation.

The exposure time of the treated skin to daylight as light radiation is preferably at least 3 minutes. Preferably, this exposure time may range from 3 minutes to 12 hours, especially between 5 minutes and 90 minutes, better still between 10 minutes and 30 minutes, regardless of the order of the steps (one before the other or simultaneous).

By way of example, in the case of simultaneous application of daylight and of the composition comprising the polysaccharide bearing a grafted uronic acid unit, the light-exposure time may advantageously range from 3 minutes to 12 hours. It is possible to perform rinsing of the composition.

By way of example, in the case of application of the composition comprising the polysaccharide bearing a grafted uronic acid unit, followed by exposure to daylight, the light-exposure time may advantageously be between 3 minutes and 12 hours. It is possible to leave the composition according to the invention in place for a period of 1 second to 3 hours, before performing the step of exposure to light radiation.

It is possible to perform rinsing of the composition, after the step of exposure to light radiation, but this is not obligatory.

The step of exposure to light radiation may be repeated several times during the day.

The application of the cosmetic composition used according to the invention is performed according to the usual techniques, for example by application (especially of creams, gels, sera or lotions) to the skin intended to be treated, in particular facial and/or neck skin, especially the skin of the area around the eyes. In the context of this process, the composition may, for example, be a care composition.

The invention will now be described with reference to the examples that follow, which are given as non-limiting illustrations. The contents are expressed as percentage by weight.

SYNTHESIS EXAMPLE 1 (POLYMER 1): HYALURONIC ACID 34% GRAFTED WITH GROUPS BEARING AN AZIDE FUNCTION

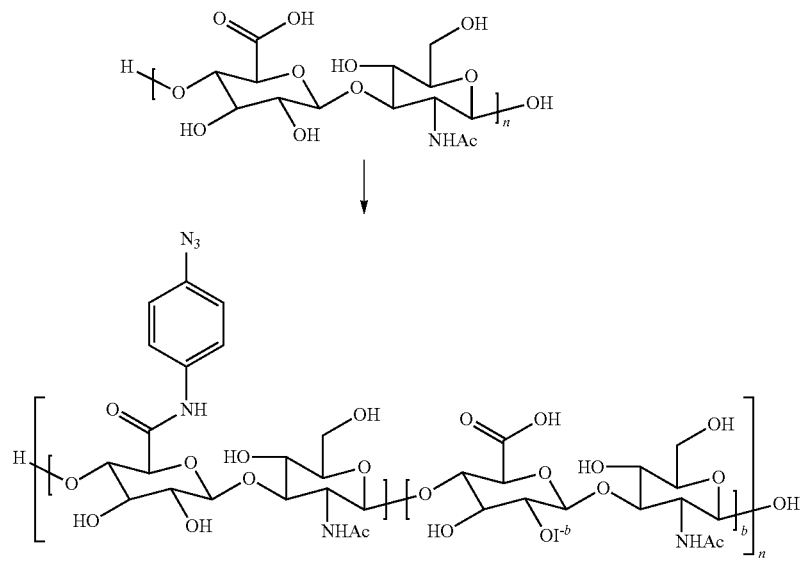

0.50 g (1.31 mmol) of hyaluronic acid (Hyacare® 50 from Evonik) was dissolved in 50 ml of distilled water in a round-bottomed flask covered with aluminium foil to prevent exposure to light. 0.16 g (1.25 mmol) of 4-azidoaniline was added, followed by addition of 0.27 g (1.24 mmol) of N-hydroxysulfosuccinimide and then addition of 0.24 g (1.25 mmol) of 1-ethyl-3-(3-dimethylaminopropyl)carbodiimide hydrochloride, with stirring at room temperature (25° C.). The pH of the reaction medium was adjusted to 4.7 by adding aqueous 0.5 M sodium hydroxide solution and aqueous 0.5 M hydrochloric acid solution. The pH was maintained for 3 hours and the flask was equipped with a stopper and stirred for 66 hours. Next, the pH was readjusted to 4.7 and the reaction was continued for 6 hours, the pH being controlled as necessary.

The reaction mixture was then introduced into a dialysis tube and dialysed in 1 liter of water for 48 hours, the water being replaced 4 times during this dialysis operation.

The residue deposited in the dialysis tube was washed/extracted with distilled water and lyophilized to obtain a fibrous yellow-coloured solid product.

This recovered solid was washed at room temperature in a round-bottomed flask (covered with aluminium foil) using acetone, for 2 hours (100 ml per extraction, 3 extractions being performed).

Washing allows the excess unreacted 4-azidoaniline to be removed. The grafted product remains insoluble in acetone.

The solid residue was then filtered off for 5 minutes and then dried under vacuum at room temperature for 12 hours. 0.51 g of a beige-coloured solid product (powder) was thus obtained.

The product was stored in an amber-coloured flask at −20° C.

The $_1$H NMR analysis in deuterated water: 34% grafting

SYNTHESIS EXAMPLE 2 (POLYMER 2): HYALURONIC ACID 40% FUNCTIONALIZED WITH AZIDE GROUPS

The polymer was prepared according to the procedure described in Synthesis Example 1, using:
0.50 g (1.31 mmol) of hyaluronic acid (Hyacare® 50 from Evonik)
0.32 g (5.50 mmol) of 4-azidoaniline
0.54 g (2.48 mmol) of N-hydroxysulfosuccinimide
0.48 g (2.50 mmol) of 1-ethyl-3-(3-dimethylaminopropyl) carbodiimide hydrochloride.

0.33 g of a beige-coloured product (powder) was obtained.

The product was stored in an amber-coloured flask at −20° C.

The $_1$H NMR analysis in deuterated water: 40% grafting

EXAMPLE 1: DEMONSTRATION OF THE TENSIONING EFFECT OF POLYMERS 1 AND 2

The following compositions were prepared:
Composition 1: aqueous solution containing 5% by weight of AM of hyaluronic acid (Hyacare® 50 from Evonik)
Composition 2: aqueous solution containing 2.5% by weight of AM of hyaluronic acid (Hyacare® 50 from Evonik)
Composition 3: aqueous solution containing 1.25% by weight of AM of hyaluronic acid (Hyacare® 50 from Evonik)
Composition 4: aqueous solution containing 0.25% by weight of AM of hyaluronic acid (Hyacare® 50 from Evonik)
Composition 5: aqueous solution containing 5% by weight of AM of polymer 1
Composition 6: aqueous solution containing 2.5% by weight of AM of polymer 1
Composition 7: aqueous solution containing 1.25% by weight of AM of polymer 1
Composition 8: aqueous solution containing 0.25% by weight of AM of polymer 1
Composition 9: aqueous solution containing 2.5% by weight of AM of polymer 2
Composition REF: aqueous composition of Hybridur® 875 polymer dispersion from Air Products (aqueous dispersion containing 40% by weight of particles of an interpenetrated network of polyurethane and acrylic polymers) at 7% AM.

The tensioning power of polymers 1 and 2 was compared in vitro with a reference tensioning polymer: Hybridur® 875 polymer dispersion from Air Products (aqueous dispersion containing 40% by weight of particles of an interpenetrated network of polyurethane and acrylic polymers) and also with reference to hyaluronic acid (Hyacare® 50 from Evonik).

The tensioning effect is measured by an in vitro retraction test. This test consists in quantifying in vitro the tensioning power of a material deposited on an elastomeric substrate (Kimtech nitrile reference 90627 from Kimberley Clark) having a modulus of about 20 MPa and a thickness of 100 μm.

26 μl of each polymer composition were deposited on a rectangular specimen (9×40 mm) of elastomer. Some of the treated specimens were irradiated for 1 minute with an Oriel sun simulator machine from the company Oriel-Lot.

After 3 hours of drying at 22±3° C. and 40±10% relative humidity, the tensioning effect exerted by the polymer deposited on the specimen is directly linked to the decrease in width at the centre of the specimen. The tensioning effect (TE1) may then be quantified in the following manner:

$$\text{tensioning effect (TE1) in \%} = (L_0 - L_1/L_0) \times 100$$

$L_0$=initial width 9 mm
and $L_1$=width after 3 hours of drying

The persistence with respect to water of the observed tensioning effect was then evaluated.

The deposits were rinsed by spraying onto the strip, at a distance of 5 cm, 10 μl of aqueous 0.9 M NaCl solution (synthetic sweat).

The deposits were dried for 3 hours at 22±3° C. and 40±10% relative humidity, and the tensioning effect after washing (TE2) was measured again by measuring the width $L_2$ of the specimen.

$$\text{Tensioning effect (TE2) in \%} = (L_0 - L_2/L_0) \times 100$$

with $L_2$=width of the specimen after rinsing and 3 hours of drying.

The following results were obtained:

| Example | Composition | Polymer | Irradiated (yes/no) | Tensioning effect (TE1) (before washing) | Tensioning effect (TE2) (after washing) |
|---|---|---|---|---|---|
| A | 1 | Hyaluronic acid | No | 33% | 11% |
| B | 2 | Hyaluronic acid | No | 22% | 0% |
| C | 3 | Hyaluronic acid | No | 0% | 0% |
| D | 4 | Hyaluronic acid | No | 0% | 0% |
| E | 5 | Polymer 1 | No | 33% | 11% |
| F | 6 | Polymer 1 | No | 22% | 0% |
| G | 7 | Polymer 1 | No | 0% | 0% |
| H | 8 | Polymer 1 | No | 0% | 0% |
| I | 5 | Polymer 1 | Yes | 77% | 77% |
| J | 6 | Polymer 1 | Yes | 77% | 77% |
| K | 7 | Polymer 1 | Yes | 44% | 44% |
| L | 8 | Polymer 1 | Yes | 0% | 0% |
| M | 9 | Polymer 2 | No | 33% | 11% |
| N | 9 | Polymer 2 | Yes | 77% | 77% |
| O | REF | Hybridur ® 875 polymer dispersion | No | 55% | 22% |

The results obtained show that the polymer of Example 1 and that of Example 2 according to the invention, after irradiation of the deposit (Examples I to L and N), make it possible to obtain a good tensioning effect before and after washing. The tensioning effect obtained thus shows good persistence with respect to water.

SYNTHESIS EXAMPLE 3 (POLYMER 3): HYALURONIC ACID FUNCTIONALIZED WITH 16% DIAZIRINE 12.8 g (34.7 mmol) of hyaluronic acid (Hyacare® 50 from Evonik) were dissolved in 1 liter of distilled water in a round-bottomed flask covered with aluminium foil to prevent exposure to light. 9.4 g (34.7 mmol) of N-{4-[3-(trifluoromethyl)-3H-diazirin-3-yl]phenyl}ethane-1,2-diamine were dissolved in 500 ml of distilled water and then added to the round-bottomed flask containing the hyaluronic acid. The pH was adjusted to 6.5 with hydrochloric acid (2M) and 12.5 g (52 mmol) of 4-(4,6-dimethoxy-1,3,5-triazin-2-yl)-4-methylmorpholinium chloride (DMTMM) were then added. The reaction mixture was stirred for 16 hours while maintaining the pH at 6.5 with hydrochloric acid (2M) or sodium bicarbonate (2M). 12.5 g (52 mmol) of DMTMM were added. The reaction mixture was stirred for

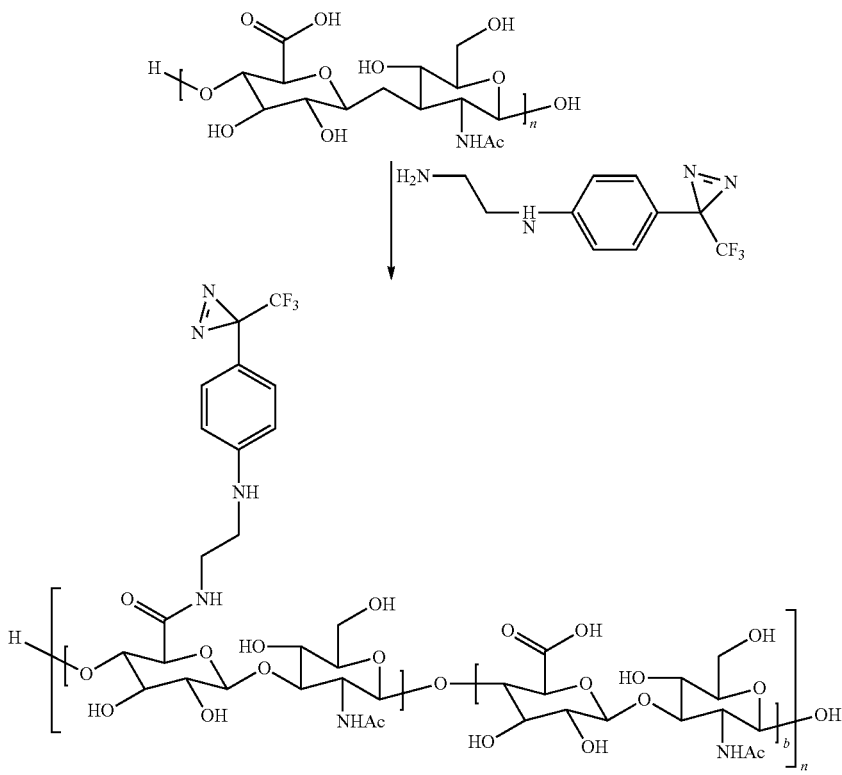

24 hours while maintaining the pH at 6.5 with hydrochloric acid (2M) or sodium bicarbonate (2M). The reaction mixture was placed in dialysis tubes (Spectra/Por Dialysis Membrane MWCO 3500) and then dialysed with distilled water (2 liters) for 48 hours. The water was changed 4 times during the 48 hours. The content of the tubes was lyophilized to generate a solid residue. The solid residue was then triturated twice with acetone (500 mL), filtered off for 5 minutes and then dried under vacuum at room temperature for 12 hours. 16 g of a beige-coloured solid product (powder) were thus obtained.

The product was stored in an amber-coloured flask at −20° C.

The $_1$H NMR analysis in deuterated water: 16% grafting

EXAMPLE 2: DEMONSTRATION OF THE TENSIONING EFFECT OF POLYMER 3

The following composition was prepared:
Composition 10: aqueous solution containing 2.5% by weight of AM of polymer 3

The tensioning effect was evaluated according to the procedure as described in Example 1, using the amounts indicated below.

The following results were obtained:

| Example | Composition | Polymer | Irradiated (yes/no) | Tensioning effect (TE1) (before washing) | Tensioning effect (TE2) (after washing) |
|---|---|---|---|---|---|
| P | 10 (30 µl) | Polymer 3 | No | 44% | 22% |
| Q | 10 (30 µl) | Polymer 3 | Yes | 66% | 66% |
| R | 10 (60 µl) | Polymer 3 | Yes | 77% | 77% |

The results obtained show that the polymer 3, after irradiation, has a good tensioning effect which is persistent with respect to water.

SYNTHESIS EXAMPLE 4 (POLYMER 4): ALGINIC ACID FUNCTIONALIZED WITH 10% DIAZIRINE

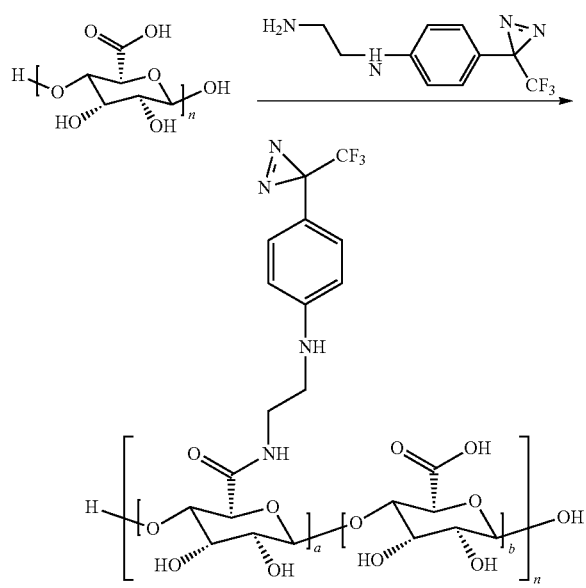

0.65 g of alginic acid (Protanal PH 6160 from the company FMC Corporation) was dissolved in 33 ml of water. The pH was adjusted to 3.5 with hydrochloric acid solution (0.2M, 10 mL). Next, a solution of 0.71 g of 1-ethyl-3-(3-dimethylaminopropyl)carbodiimide hydrochloride in 3 ml of water was added, with stirring at room temperature (25° C.). After 5 minutes of stirring, 0.8 g of N-hydroxysulfosuccinimide was added, the reaction mixture was stirred for 5 minutes at room temperature, and 1 g of N-{4-[3-(trifluoromethyl)-3H-diazirin-3-yl]phenyl}ethane-1,2-diamine was then added. After 5 minutes, the pH was adjusted to 4.7 with hydrochloric acid solution (0.4M). The reaction mixture was stirred for 40 hours at room temperature and protected from light. Next, the reaction mixture was poured into acetone (300 ml), stirred for 1 hour at room temperature and then filtered to recover a white solid. The solid was placed in water (40 mL) and then dialysed with water for 3 days, the water being changed each day. The product was obtained by lyophilization. 0.6 g of a beige-coloured solid product (powder) was thus obtained.

The product was stored in an amber-coloured flask at −20° C.

The $_1$H NMR analysis in deuterated water: 10% grafting

SYNTHESIS EXAMPLE 5 (POLYMER 5): ALGINIC ACID FUNCTIONALIZED WITH 6% DIAZIRINE

The polymer was prepared according to the procedure described in Synthesis Example 4, using:
0.65 g of alginic acid in 33 ml of water
0.5 g of N-{4-[3-(trifluoromethyl)-3H-diazirin-3-yl]phenyl}ethane-1,2-diamine
0.4 g of N-hydroxysulfosuccinimide
0.36 g of 1-ethyl-3-(3-dimethylaminopropyl)carbodiimide. hydrochloride in 3 mL of water
0.57 g of a beige-coloured product (powder) was obtained.

The product was stored in an amber-coloured flask at −20° C.

The $_1$H NMR analysis in deuterated water: 6% grafting

EXAMPLE 3: DEMONSTRATION OF THE TENSIONING EFFECT OF POLYMERS 4 AND 5

The following composition was prepared:
Composition 11: aqueous solution containing 1% by weight of AM of polymer 4
Composition 12: aqueous solution containing 1% by weight of AM of polymer 5

The tensioning effect was evaluated according to the procedure as described in Example 1, using the amounts indicated below.

The following results were obtained:

| Example | Composition | Polymer | Irradiated (yes/no) | Tensioning effect (TE1) (before washing) | Tensioning effect (TE2) (after washing) |
|---|---|---|---|---|---|
| S | 11 (30 µl) | Polymer 4 | No | 55% | 11% |
| T | 11 (30 µl) | Polymer 4 | Yes | 55% | 55% |
| U | 12 (30 µl) | Polymer 5 | No | 55% | 11% |
| V | 12 (30 µl) | Polymer 5 | Yes | 66% | 55% |

The results obtained show that the polymers 4 and 5, after irradiation, have a good tensioning effect which is persistent with respect to water.

EXAMPLE 4

An antiwrinkle gel having the following composition is prepared:

| | |
|---|---|
| polymer of Example 1 | 1 g |
| hydroxyethylcellulose (Natrosol ® 250 HHR CS from Ashland) | 0.5 g |
| Preserving agents | qs |
| Water | qs 100 g |

The composition obtained is applied to the face and the surface of the treated skin is then irradiated with white light (Lite-Pad lamp from the company Reicorp) for 3 minutes. The treatment applied makes it possible to effectively smooth out the wrinkles.

EXAMPLE 5

An antiwrinkle gel having the following composition is prepared:

| | |
|---|---|
| Polymer of Example 2 | 1 g |
| Hydroxyethylcellulose (Natrosol ® 250 HHR CS from Ashland) | 0.5 g |
| Preserving agents | qs |
| Water | qs 100 g |

The composition obtained is applied to the face and the surface of the treated skin is then irradiated with white light (Lite-Pad lamp from the company Reicorp) for 10 minutes. The treatment applied makes it possible to effectively smooth out the wrinkles.

EXAMPLE 6

An antiwrinkle gel having the following composition is prepared:

| | |
|---|---|
| polymer of Example 3 | 1 g |
| hydroxyethylcellulose (Natrosol ® 250 HHR CS from Ashland) | 0.5 g |
| Preserving agents | qs |
| Water | qs 100 g |

The composition obtained is applied to the face and the surface of the treated skin is then irradiated with white light (Lite-Pad lamp from the company Reicorp) for 10 minutes. The treatment applied makes it possible to effectively smooth out the wrinkles.

EXAMPLE 7

An antiwrinkle gel having the following composition is prepared:

| | |
|---|---|
| polymer of Example 4 | 1 g |
| hydroxyethylcellulose (Natrosol ® 250 HHR CS from Ashland) | 0.3 g |
| Preserving agents | qs |
| Water | qs 100 g |

The composition obtained is applied to the face and the surface of the treated skin is then irradiated with blue light (goLITE BLU from the company Philips) for 15 minutes. The treatment applied makes it possible to effectively smooth out the wrinkles.

EXAMPLE 8

An antiwrinkle gel having the following composition is prepared:

| | |
|---|---|
| polymer of Example 5 | 1.5 g |
| hydroxyethylcellulose (Natrosol ® 250 HHR CS from Ashland) | 0.2 g |
| Preserving agents | qs |
| Water | qs 100 g |

The composition obtained is applied to the face and the surface of the treated skin is then irradiated with blue light (Camag Box 3 lamp from the company Camag) for 5 minutes. The treatment applied makes it possible to effectively smooth out the wrinkles.

The invention claimed is:

1. A cosmetic process for caring for skin comprising:
   (i) a step consisting in applying to the skin a cosmetic composition comprising, in a physiologically acceptable medium, at least 0.3% by weight, relative to the total weight of the composition, of a grafted polysaccharide polymer of formula:

PS—(CO—NH-L-X)$_a$(COOH)$_b$

in which PS denotes a basic backbone of a polysaccharide bearing carboxylic acid groups;
   L is a linear, branched or cyclic, saturated or unsaturated divalent hydrocarbon-based group comprising from 1 to 20 carbon atoms, wherein said divalent hydrocarbon-based group may optionally be interrupted with one or more non-adjacent heteroatoms chosen from sulfur, oxygen, or a group chosen from —NH—, —COO—, —CONH—, —O—CO—NH— or —NH—CO—NH—, and wherein said divalent hydrocarbon-based group optionally comprises one or more groups chosen from hydroxyl, amine, thiol, carboxylic acid, amide and cyano groups;
   X denotes an azide or diazirine photoactive group;
   (a) denotes a content of COOH groups of the polysaccharide that are substituted with the group —NH-L-X;
   (b) denotes a content of unsubstituted COOH groups of the polysaccharide;
   (a) being between 0.01 and 0.8; (b) being between 0.2 and 0.99; and (a+b)=1; and
   (ii) a step consisting in exposing the skin to light radiation.

2. The process according to claim 1, wherein the polysaccharide comprises one or more base units chosen from uronic acid, glucuronic acid and mannuronic acid.

3. The process according to claim 1, wherein the polysaccharide is chosen from hyaluronic acid, chondroitin, chondroitin sulfate, alginic acid, heparin, heparin sulfate and xanthan gum.

4. The process according to claim 1, wherein the polysaccharide is hyaluronic acid.

5. The process according to claim 1, wherein a (a) is between 0.1 and 0.6 and (b) is between 0.4 and 0.9.

6. The process according to claim 1, wherein the group L is chosen from the following groups:

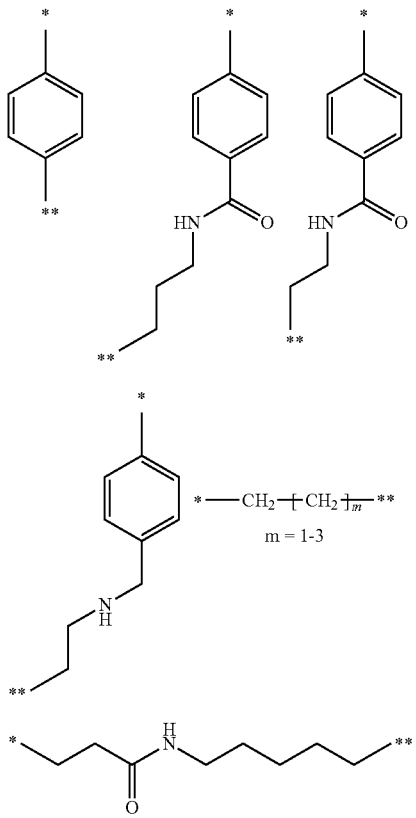

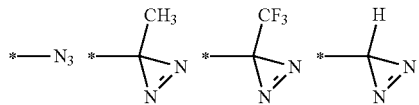

wherein (\*) represents the bond with the photoactive group X, and wherein (\*\*) represents the bond with the amide group of the polymer.

7. The process according to claim 1, wherein the photoactive group X is chosen from the following groups:

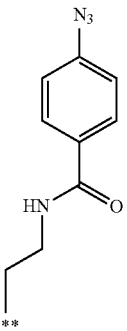

wherein (\*) represents the bond with the group L.

8. The process according to claim 1, wherein the group X-L- is chosen from:

(i)

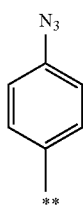

-continued (ii)

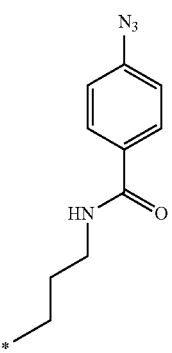

(iii)

(iv)

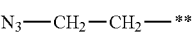

(v)

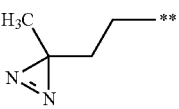

(vi)

(vii)

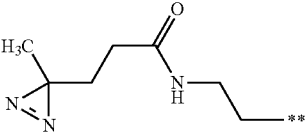

(viii)

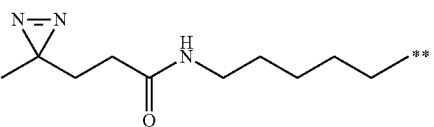

(ix)

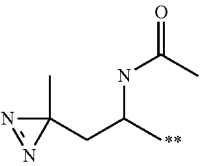

-continued (x)
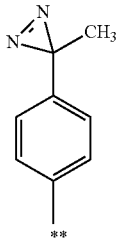

(xi)
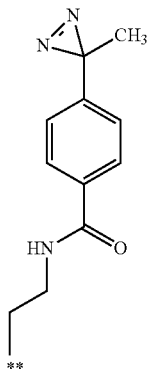

(xii)
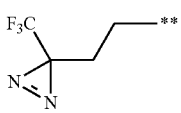

(xiii)
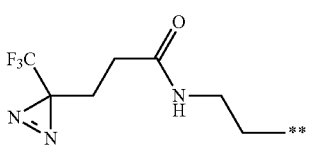

(xiv)
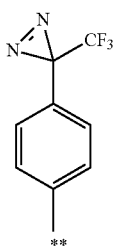

(xv)
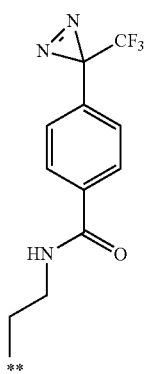

wherein (**) represents the bond with the amide group of the polymer.

9. The process according to claim 1, wherein the grafted polysaccharide polymer has a weight-average molecular weight ranging from 5,000 daltons to 1,000,000 daltons determined by liquid chromatography, using 0.1 M sodium chloride and 330 mg/l of sodium azide in water as eluent, with dextran as standard, and using Wyatt Optilab T-Rex refractometer and Wyatt Dawn-Heleos II light scattering detectors.

10. The process according to claim 1, wherein the grafted polysaccharide polymer is present in the composition in a content ranging from 0.3% to 10% by weight, relative to the total weight of the composition.

11. The process according to claim 10, wherein the step (ii) consisting in exposing the skin to light radiation is performed after or at the same time as the step (i) consisting in applying to the skin the cosmetic composition.

12. The process according to claim 10, wherein the step (ii) consisting in exposing the skin to light radiation is performed after the step (i) consisting in applying to the skin the cosmetic composition.

13. The process according to claim 1, wherein the light radiation is natural light or artificial light with a wavelength of between 360 nm and 600 nm.

14. The process according to claim 1, in which the light radiation has a source chosen from arc lamps, fluorescent lamps, incandescent lamps, light emitting diodes and lasers.

15. The process according to claim 1, wherein exposure time of the skin to the light radiation in step (ii) is at least 5 seconds.

16. The process according to claim 1, wherein the composition is in the form of an oil-in-water emulsion or an aqueous gel.

17. The process according to claim 1, wherein the cosmetic composition is applied to wrinkled skin for attenuating wrinkles.

18. A grafted polysaccharide polymer of formula:

PS—(CO—NH-L-X)$_a$(COOH)$_b$ in which PS denotes a basic backbone of a polysaccharide bearing carboxylic acid groups;
L is a linear, branched or cyclic, saturated or unsaturated divalent hydrocarbon-based group comprising from 1 to 20 carbon atoms, wherein said divalent hydrocarbon-based group may optionally be interrupted with one or more non-adjacent heteroatoms chosen from sulfur, oxygen, or a group chosen from —NH—, —COO—, —O—CO—NH— or —NH—CO—NH—, and wherein said divalent hydrocarbon-based group optionally comprises one or more groups chosen from hydroxyl, amine, thiol, carboxylic acid, amide and cyano groups;
X denotes a diazirine photoactive group;
(a) denotes a content of COOH groups of the polysaccharide that are substituted with the group —NH-L-X;
(b) denotes a content of unsubstituted COOH groups of the polysaccharide;
(a) being between 0.01 and 0.8; (b) being between 0.2 and 0.99, and (a+b)=1.

19. The grafted polysaccharide polymer according to claim 18, wherein the polysaccharide comprises one or more base units chosen from uronic acid, glucuronic acid and mannuronic acid.

20. The grafted polysaccharide polymer according to claim 18, wherein the polysaccharide is chosen from hyaluronic acid, chondroitin, chondroitin sulfate, alginic acid, heparin, heparin sulfate and xanthan gum.

21. The grafted polysaccharide polymer according to claim 18, wherein the polysaccharide is hyaluronic acid.

22. The grafted polysaccharide polymer according to claim 18, wherein a (a) is between 0.1 and 0.6 and (b) is between 0.4 and 0.9.

23. The grafted polysaccharide polymer according to claim 18, wherein the group L is chosen from the following groups:

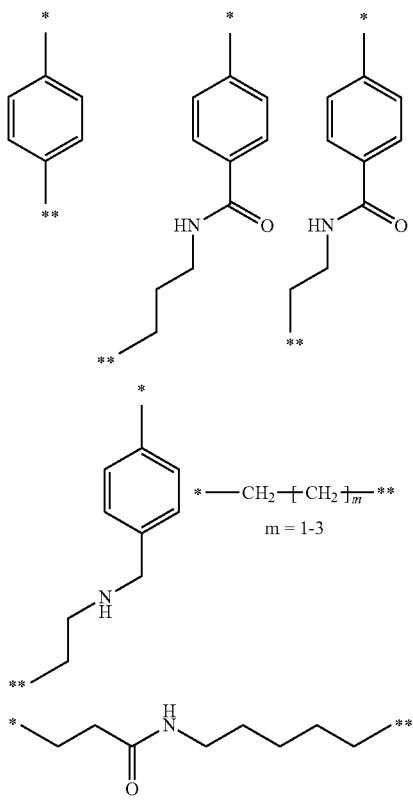

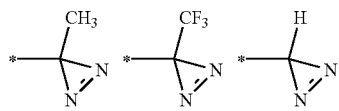

wherein (*) represents the bond with the photoactive group X, and wherein (**) represents the bond with the amide group of the polymer.

24. The grafted polysaccharide polymer according to claim 18, wherein the photoactive group X may be chosen from the following groups:

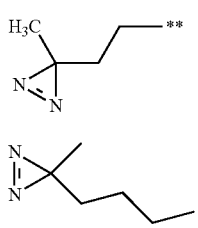

wherein (*) represents the bond with the photoactive group L.

25. The grafted polysaccharide polymer according to claim 18, wherein the group X-L- is chosen from:

(v)

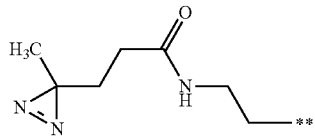

(vi)

(vii)

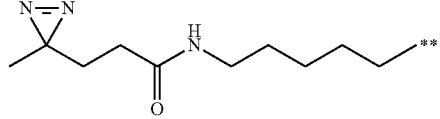

(viii)

(ix)

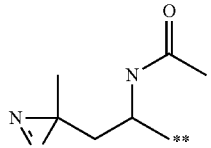

(x)

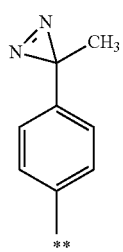

(xi)

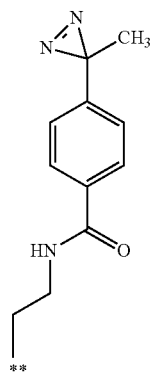

(xii)

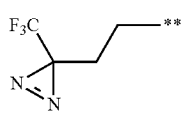

(xiii)

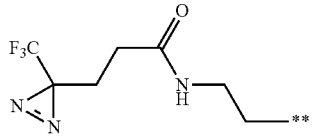

(xiv)

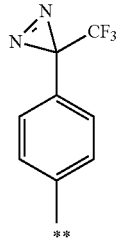

-continued

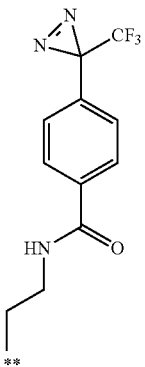

(xv)

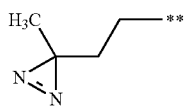

wherein (**) represents the bond with the amide group of the polymer.

26. The grafted polysaccharide polymer according to claim 18, wherein the grafted polysaccharide polymer has a weight-average molecular weight ranging from 5,000 daltons to 1,000,000 daltons determined by liquid chromatography, using 0.1 M sodium chloride and 330 mg/l of sodium azide in water as eluent, with dextran as standard, and using Wyatt Optilab T-Rex refractometer and Wyatt Dawn-Heleos II light scattering detectors.

27. A composition comprising, in a physiologically acceptable medium, the grafted polysaccharide polymer according to claim 18.

28. The composition according to claim 27, wherein the grafted polysaccharide polymer is present in a content ranging from 0.3% to 10% by weight, relative to the total weight of the composition.

29. The composition according to claim 27, further comprising a cosmetic adjuvant chosen from water, emulsifiers, preserving agents, sequestrants, fragrances, thickeners, oils, waxes and film-forming polymers.

30. The composition according to claim 27, which is in the form of an oil-in-water emulsion or an aqueous gel.

* * * * *